(12) United States Patent
Haddad et al.

(10) Patent No.: US 8,981,140 B1
(45) Date of Patent: Mar. 17, 2015

(54) PERIPHERALLY AROMATIC SILSESQUIOXANES FEATURING REACTIVE FUNCTIONALITY: SYNTHESIS AND APPLICATIONS THEREOF

(75) Inventors: Timothy Haddad, Lancaster, CA (US); Joseph Mabry, Lancaster, CA (US); Gregory Yandek, Tehachapi, CA (US); Vandana Vij, Palmdale, CA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 667 days.

(21) Appl. No.: 13/210,915

(22) Filed: Aug. 16, 2011

Related U.S. Application Data (60) Provisional application No. 61/374,669, filed on Aug. 18, 2010.

(51) Int. Cl.
*C07F 7/00* (2006.01)

(52) U.S. Cl.
USPC .......................... 556/460; 556/455; 556/461

(58) Field of Classification Search
CPC ................................. C07F 7/0874; C07F 7/21
USPC .......................................... 556/455, 460, 461
See application file for complete search history.

(56) References Cited

U.S. PATENT DOCUMENTS

| | | | |
|---|---|---|---|
| 2,687,424 A | 8/1957 | Sommer | |
| 3,382,279 A | 5/1968 | Niderprum | |
| 3,465,017 A | 9/1969 | Coutant | |
| 4,709,008 A | 11/1987 | Shimp | |
| 4,774,028 A | 9/1988 | Imai et al. | |
| 5,258,534 A | 11/1993 | Larson et al. | |
| 5,283,348 A | 2/1994 | Bank | |
| 5,284,968 A | 2/1994 | Craig, Jr. | |
| 5,629,394 A | 5/1997 | Cheradame et al. | |
| 5,912,377 A | 6/1999 | Hall et al. | |
| 6,057,402 A | 5/2000 | Zhou et al. | |
| 6,217,943 B1 | 4/2001 | Hall et al. | |
| 6,489,380 B1 | 12/2002 | Zhou et al. | |
| 6,716,919 B2 | 4/2004 | Lichtenhan et al. | |
| 6,767,930 B1 | 7/2004 | Svejda et al. | |
| 6,770,724 B1 | 8/2004 | Lichtenhan et al. | |
| 6,844,379 B2 | 1/2005 | Zhou et al. | |
| 7,053,167 B2 | 5/2006 | Ito et al. | |
| 7,193,015 B1 | 3/2007 | Mabry et al. | |
| 7,291,747 B2 | 11/2007 | Oikawa et al. | |
| 7,332,822 B2 | 2/2008 | Basheer | |
| 7,790,841 B1 | 9/2010 | Yandek et al. | |
| 7,897,667 B2 | 3/2011 | Mabry et al. | |
| 8,058,380 B1 | 11/2011 | Vij et al. | |
| 8,276,664 B2 | 10/2012 | Gupta | |
| 8,557,329 B2 | 10/2013 | Dai et al. | |
| 8,565,892 B2 | 10/2013 | Nayfach-Battilar | |
| 8,580,027 B1 | 11/2013 | Campos et al. | |
| 8,741,432 B1 | 6/2014 | Campos et al. | |
| 2001/0016616 A1 | 8/2001 | Yeager et al. | |
| 2005/0009982 A1* | 1/2005 | Inagaki et al. | 524/588 |
| 2006/0194068 A1* | 8/2006 | Katoh et al. | 428/447 |
| 2007/0173657 A1 | 7/2007 | Chen et al. | |
| 2008/0199805 A1 | 8/2008 | Ruskin et al. | |
| 2009/0069508 A1 | 3/2009 | Poe et al. | |
| 2009/0176097 A1 | 7/2009 | Brown et al. | |
| 2010/0063244 A1 | 3/2010 | Poe et al. | |
| 2010/0068168 A1 | 3/2010 | Song et al. | |
| 2010/0098761 A1 | 4/2010 | Song et al. | |
| 2010/0159011 A1 | 6/2010 | Lian et al. | |
| 2010/0280561 A1 | 11/2010 | Song et al. | |
| 2012/0000853 A1 | 1/2012 | Tuteja et al. | |
| 2012/0015191 A1 | 1/2012 | Treadway | |
| 2012/0190532 A1 | 7/2012 | Celiker et al. | |
| 2012/0214269 A1 | 8/2012 | Harding | |

FOREIGN PATENT DOCUMENTS

CN 102659827 9/2012

OTHER PUBLICATIONS

Seurer et al, Polymer Preprints (American Chemical Society, Division of Polymer Chemistry) (2009), 50(2), 820-821.*
Fina, A., et al., "Polyhedral Oligomeric Silsesquioxanes (POSS) Thermal Degradation," Thermochimica Acta 440, pp. 36-42 (Nov. 14, 2005).
Brian M. Moore et al., "Asymmetric aryl polyhedral oligomeric silsequioxanes (ArPOSS) with enhanced solubility," Journal of Organometallic Chemistry, vol. 696 (2011) pp. 2676-2680.
P.D. Lickiss and F. Rataboul, Chapter 1: "Fully condensed polyhedral oligosilsesquioxanes (POSS): From synthesis to application," Adv. Organomet. Chem. vol. 57 (2008) pp. 1-116.

(Continued)

*Primary Examiner* — Sudhakar Katakam
(74) *Attorney, Agent, or Firm* — AFMCLO/JAZ; Chastity Whitaker (57) ABSTRACT

Novel POSS mono- and dianiline compounds, their synthesis procedures, and applications in host materials for the purposes of property enhancement are described. This class of POSS compounds features completely aromatic peripheries and partial amine functionality for facile and controlled reactive incorporation into a variety of polymers, and further utility may be derived from reactions of the available amine groups with anhydrides such as phenylethynyl phthalic anhydride (PEPA) to form reactive imide-type oligomers for incorporation into high performance thermosetting polymers. Modification of polymer hosts with the subject nanoparticles can result in a variety of property improvements including mechanical, thermal, tribological, electrical, as well as improved moisture resistance.

10 Claims, 3 Drawing Sheets

(56) References Cited

OTHER PUBLICATIONS

J. D. Lichtenhan et al., "Linear hybrid polymer building blocks: methacrylate-functionalized polyhedral oligomeric silsesquioxane monomers and polymers," Macromol. vol. 28 (1995) 8435-8437.

S.D. Rosenberg et al., "Preparation of Some Arylchlorosilanes with Arylmagnesium Chlorides" Journal Organomet. Chemistry vol. 22 (1957) pp. 1606-1607.

P. Iyer and M. R. Coleman, "Thermal and Mechanical Properties of Blended Polyimide and Amine-Functionalized Poly(orthosiloxane) Composites," Journal of Applied Polymer Science, vol. 108 (2008) pp. 2691-2699.

G. R. Yandek et al., "Effects of Peripheral Architecture on the Properties of Aryl Polyhedral Oligomeric Silsesquioxanes," J. Phys. Chem. vol. 116, (2012) pp. 16755-16765.

S. S. Chhatre et al., "Fluoroalkylated Silicon-Containing Surfaces—Estimation of Solid-Surface Energy," Appl. Mater. Interfaces. vol. 2 (2010) 3544-3554.

F. J. Feher et al., "A new route to heterosilsesquioxane frameworks," Angew. Chem., Int. Ed. vol. 37 (1998) 2663-2667.

F. J. Feher et al., "A new route to incompletely-condensed silsesquioxanes: acid-mediated cleavage and rearrangement of (c-C6H11)6Si6O9 to C2-[(c-C6H11)6Si6O8X2]," Chem. Commun. (1999) 1705-1706.

F. J. Feher et al., "A new route to incompletely-condensed silsesquioxanes: base-mediated cleavage of polyhedral oligosilsesquioxanes," Chem. Commun. (1999) 2309-2310.

F. J. Feher, "Controlled cleavage of R8Si8O12 frameworks: a revolutionary new method for manufacturing precursors to hybrid inorganic-organic materials," Chem. Commun. (1998) 399-400.

A. Tuteja et al., "Designing superoleophobic surfaces," Science. vol. 318 (2007) 1618-1622.

S. H. Phillips et al., "Developments in nanoscience: polyhedral oligomeric silsesquioxane (POSS)-polymers," Current Opinion in Solid State and Materials Science. vol. 8 (2004) 21-29.

W. Choi et al., "Fabrics with tunable oleophobicity," Adv. Mater. vol. 21 (2009) 2190-2195.

S. T. Iacono et al., "Facile synthesis of hydrophobic fluoroalkyl functionalized silsesquioxane nanostructures," Chem. Commun. (2007) 4992-4994.

J. M. Mabry et al., "Fluorinated polyhedral oliomeric silsesquioxanes (F-POSS)," Angew. Chem., Int. Ed. vol. 47 (2008) 4137-4140.

E. G. Shockey et al., "Functionalized polyhedral oligosilsesquioxane (POSS) macromers: new graftable POSS hydride, POSS α-olefin, POSS epoxy, and POSS chlorosilane macromers and POSS-siloxane triblocks," Appl. Organomet. Chem. vol. 13 (1999) 311-327.

R. Duchateau "Incompletely condensed silsesquioxanes: versatile tools in developing silica-supported olefin polymerization catalysts," Chem. Rev. vol. 102 (2002) 3525-3542.

C. Ohde et al., "Oxovandaium (IV) silsesquioxane complexes," Inorg. Chem. vol. 49 (2010) 2479-2485.

K. Pielichowski et al., "Polyhedral oligomeric silsesquioxane (POSS)-containing nanohybrid polymers," J. Adv. Polym. Sci. vol. 201 (2006) 225-296.

F. J. Feher et al., "Practical methods for synthesizing four incompletely condense silsesquioxanes from a single R8Si8O12 framework," Chem. Commun. (1998) 1279-1280.

D. B. Cordes et al., "Recent developments in the chemistry of cubic polyhedral oligosilsesquioxanes," Chem. Rev. vol. 110 (2010) 2081-2173.

T. Haddad et al, "Polyhedral Oligomeric Silsequioxane (POSS)-Styrene Macromers" Organomet. vol. 11 (2001) 155-164.

A. Tuteja et al., "Robust omniphobic surfaces," PNAS. vol. 105 (2008) 18200-18205.

R. H. Baney et al., "Silsesquioxanes," Chem. Rev. vol. 95 (1995) 1409-1431.

F. J. Feher et al., "Synthesis and structural characterization of a remarkably stable, anionic, incompletely condensed silsesquioxane framework," Chem. Commun. (1997) 829-830.

H. Liu et al., "A spectroscopic investigation of incompletely condensed polyhedral oligomeric silisesquioxanes (POSS-mono-ol, POSS-diol and POSS-triol): hydrogen-bonded interaction and host-guest complex," J. Organomet. Chem. vol. 693 (2008) 1301-1308.

T.W. Dijkstra et al., "Silsesquioxane models for geminal silica surface silanol sites. A spectroscopic investigation of different types of silanols," J. Am. Chem. Soc. vol. 124 (2002) 9856-9864.

S. T. Iacono et al., "Preparation of composite fluoropolymers with enhanced dewetting using fluorinated silsesquioxanes as drop-in modifiers," J. Mater. Chem. vol. 20 (2010) 2979-2984.

F. J. Feher et al., "Facile framework cleavage reactions of a completely condensed silsesquioxane framework," J. Am. Chem. Soc. vol. 119 (1997) 11323-11324.

F. J. Feher et al., "Reactions of incompletely-condensed silsequioxanes with pentamethylantimony: a new synthesis of metal-lasilsesquioxanes with important implications for the chemistry of silica surfaces," J. Am. Chem. Soc. vol. 114 (1992) 3859-3866.

F. J. Feher and T. L. Tajima, "Synthesis of a molybdenum-containing silsesquioxane which rapidly catalyzes the metathesis of olefins," J. Am. Chem. Soc. vol. 116 (1994) 2145-2146.

F. J. Feher et al., "Silsesquioxanes as models for silica surfaces," J. Am. Chem. Soc. vol. 111 (1989) 1741-1748.

H. M. Cho et al., "A Mo(VI) alkylidyne complex with polyhedral oligomeric silsesquioxane ligands: homogeneous analogue of a silica-supported alkyne metathesis catalyst," J. Am. Chem. Soc. vol. 128 (2006) 14742-14743.

United States Patent and Trademark Office, Non-Final Office Action in U.S. Appl. No. 13/624,151, mailed Nov. 7, 2013, 12 pages total.

T. S. Haddad and J. D. Lichtenhan, "Hybrid organic-inorganic thermoplastics: styryl-based polyhedral oligomeric silsesquioxane polymers," Macromol. vol. 29 (1996) 7302-7304.

K. Koh et al., "Precision synthesis of a fluorinated polyhedral oligomeric silsesquioxane-terminated polymer and surface characterization of its blend film with poly(methyl methacrylate)," Macromol. vol. 38 (2005) 1264-1270.

E. Lucenti et al., "Synthesis and characterization of osmium-containing silsesquioxanes: high-yield routes to {Os3(CO)10(μ-H)[μ-O)Si7O10(c-C6H11)7]} and the new clusters {Os3(CO)10(μ-H)[μ-O)Si7O9(OH)2(c-C6H11)7]}, {[Os3(CO)10(μ-H)]2[μ-O)2Si7O9(OH)(c-C6H11)7}, {Os3(CO)10(μ-H)μ-O)Si8O11(OH)(c-C6H11)8]}, and {[Os3(CO)10(μ-H)] 2(μ-O)2Si8O11(c-C6H11)8}," Organomet. vol. 26 (2006) 75-82.

K. Wada et al., "Synthesis and catalytic activity of group 4 metallocene containing silsesquioxanes bearing functionalized silyl groups," Organomet. vol. 23 (2004) 5824-5832.

K. Ohno et al., "Living radical polymerization by polyhedral oligomeric silsesquioxane-holding initiators; precision synthesis of tadpole-shaped organic/inorganic hybrid polymers," Macromol. vol. 37 (2004) 8517-8522.

S. T. Iacono et al, "Synthesis, characterization, and surface morphology of pendant polyhedral oligomeric silsesquioxane perfluorocyclobutyl aryl ether copolymers," Macromol. vol. 40 (2007) 9517-9522.

Sean M. Ramirez, "Synthesis and Free Radical Polymerization of Fluorinated Polyhedral Oligomeric Silsesquioxane (F-POSS) Macromers: Precursors for Low Surface Energy Materials," Presentation to the Chemistry Department of the Air Force Academy, Colorado Springs, Colorado, Apr. 12, 2012.

R. Duchateau et al, "Silica-Grafted Diethylzinc and a Silsesquioxane-Based Zinc Alkyl Complex as Catalysts for the Alternating Oxirane-Carbon Dioxide Copolymerization," Organomet. vol. 26 (2007) 4204-4211.

Michael E Wright, Chemical Modification of Fluorinated Polyimides: New Thermally Curing Hybrid Polymers with POSS, Macromolecules 2006, pp. 4710-4718.

A. Fina et al., "POSS-based hybrids by melt/reactive blending," J. Mater. Chem., vol. 20 (2010) 9297-9305.

Badrinarayana et al., "Zirconium tungstate/cyanate ester nanocomposites with tailored thermal expansion," Comp. Sci. & Tech., vol. 71 (2011) 1385-1391.

Brenier, "Bifunctional surfaces with superhydrophobic and plasmonic properties," J. Phys. Chem. C., vol. 115 (2011) 10544-10549.

(56) References Cited

OTHER PUBLICATIONS

Campos et al., "Fluoroalkyl-functionalized silica particles: synthesis, characterization, and wetting characteristics," Langmuir, vol. 27 (2011) 10206-10215.
Hamerton et al., "Studies on a dicyanate containing four phenylene rings and polyacryanurate blends. 2. Application of mathematical models to the catalysed polymerization process," Polymer., vol. 44 (2003) 4839-4852.
Hudson and Nelson, University Physics 2d ed. 754 (Saunders College Publishing: Philadelphia 1990), p. 754.
Machine Translation, Chinese Patent Publication No. 102659827A (2012), 9 pages total.
Ogawa et al., "Development of a transparent and ultrahydrophobic glass plate," Jpn. J. Appl. Phys., vol. 32 (1993) L614-L615.
Sagiv, "Organized monolayers by adsorption. 1. Formation and structure of oleophobic mixed monolayers on solid surfaces," JACS, vol. 102 (1980) 92-98.
Zhao et al., "Autocatalytic curing kinetics of thermosetting polymers: a new model based on temperature dependent reaction orders," Polymer, vol. 51 (2010) 3814-3820.
United States Patent and Trademark Office, Non-Final Office Action in U.S. Appl. No. 13/624,355, mailed Sep. 24, 2014, 7 pages total.
Moore et al., "Asymmetric aryl polyhedral oligomeric silsesquioxanes (ArPOSS) with enhanced solubility," J. Organomet. Chem., vol. 696 (2011) 2676-2680.
Moore et al., "Increasing the solubility of inert peripherally aromatic POSS," Abstracts of Papers, 241st ACS National Meeting & Exposition, Anaheim, CA (2011), POLY-225, 1 page total.
Cheng et al., "Phosphonium-containing ABA triblock copolymers: controlled free radical polymerization of phosphonium ionic liquids," Macromol., vol. 44 (2011) 6509-6517.
Destarac, "On the critical role of RAFT agent design in reversible addition-fragmentation chain transfer (RAFT) polymerization," Polymer Rev., vol. 51 (2011) 163-187.
Lu et al., "L-proline functionalized polymers prepared by RAFT polymerization and their assemblies as supported organocatalysts," Macromol., vol. 44 (2011) 7233-7241.
Ramirez et al., "Incompletely condensed fluoroalkyl silsesquioxanes and derivatives: precursors for low surface energy materials," JACS, vol. 133 (2011) 20084-20087.
Stamenovic et al., "Norbornenyl-based RAFT agents for the preparation of functional polymers via thio-ene chemistry," Macromol., vol. 44 (2011) 5619-5630.
Tan et al., "Tailoring micelle formation and gelation in (PEG-P(MA-POSS)) amphiphilic hybrid block copolymers," Macromol., vol. 44 (2011) 622-631.
Wang et al., "Hepta(3,3,3-trifluoropropyl) polyhedral oligomeric silsesquioxane-capped poly(N-isopropylacrylamide) telechelics: synthesis and behavior of physical hydrogels," ACS Appl. Mater. & Interf., vol. 3 (2011) 898-909.
Zeng et al., "Nanostructures and surface hydrophobicity of epoxy thermosets containing hepta(3,3,3-trifluoropropyl) polyhedral oligomeric silsesquioxane-capped poly(hydroxyether of bisphenol A) telechelics," J. Colloid. & Interf. Sci., vol. 363 (2011) 250-260.
Guenthner et al., "Synthesis, cure kinetics, and physical properties of a new tricyanate ester with enhanced molecular flexibility," Polymer, vol. 52 (2011) 3933-3942.
Guenthner et al., "Cure characteristics of tricyanate ester high-temperature composite resins," Presentation at SAMPE conference, Long Beach, CA (2011) 22 pages total.
United States Patent Office, "Final Office Action in U.S. Appl. No. 13/624,151," mailed May 30, 2014, 11 pages total.
United States Patent and Trademark Office, Non-Final Office Action in U.S. Appl. No. 14/013,600, mailed Aug. 22, 2014, 6 pages.
Braunecker et al., "Controlled/living radical polymerization: features, developments, and perspectives," Prog. Polym. Sci., vol. 32 (2007) 93-146.
Goto et al., "Mechanism and kinetics of RAFT-based living radical polymerization of styrene and methyl methacrylate," Macromol., vol. 34 (2001) 402-408.
Iacono et al., "Synthesis, characterization, and properties of chain terminated polyhedral oligomeric silsesquioxane-functionalized perfluorocyclobutyl aryl ehter copolymers," Polymer., vol. 48 (2007) 4637-4645.
Mayadunne et al., "Living radical polymerization with reversible addition-fragmentation chain transfer (RAFT polymerization) using dithiocarbanatesas chain transfer agents," Macromol., vol. 32 (1999) 6977-6980.
McCormic et al., "Aqueous RAFT polymerization: recent developments in synthesis of functional water-soluble (Co)polymers with controlled structures," ACC Chem. Res., vol. 37 (2004) 312-325.
Moad et al., "Toward living radical polymerization" ACC Chem. Res., vol. 41 (2008) 1133-1142.
Thomas et al., "Kinetics and molecular weight control of the polymerization of acrylamide via RAFT" Macromol., vol. 37 (2004) 8941-8950.
Tsujii et al., "Hepta(3,3,3-trifluoropropyl) polyhedral oligomeric silsesquioxane-capped poly(n-isopropylacrylamide) telechcelics: synthesis and behavior of physical hydrogels," Macromol., vol. 34 (2001) 898-909.
Zeng et al., "Rapid deswelling and reswelling response of poly(N-isopropylacrylamide) hydrogels via formation of interpenetrating polymer networks with polyhedral oligomeric silsesquioxane-capped poly(ethylene oxide) amphiliphilic telechelics," J. Phys. Chem. B., vol. 3 (2009) 11831-11840.
Zeng et al., "Organic-inorganic hybrid hydrogels involving poly(N-isopropylacrylamide) and polyhedral oligomeric silsesquioxane: preparation and rapid thermoresponsive properties," J. Polym. Sci. Part B Polym. Phys., vol. 47 (2009) 504-516.
Zhang et al., "Synthesis via RAFT polymerization of tadpole-shaped organic/inorganic hyrid poly(acrylic acid) containing polyhedral oligomeric silsesquioxane (POSS) and their self-assemlby in water," Macromol., vol. 42 (2009) 2563-2569.
Isemura et al., "Dicloropentafluoroprogane as solvents for size exclusion chromatography,"Chromatogr. A, vol. 1026 (2004) 109-116.
Crivello et al., "The synthesis, characterization, and photoinitiated cationic polymerization of silicon-containing epoxy resins," J. Poly. Sci. Part A: Polym. Chem., vol. 28 (1990) 479-503.
Georjon et al., "Effects of crosslink density on mechanical properties of high glass transition temperature polycyanurate networks," J. Appl. Polym. Sci., vol. 65 (1998) 2471-2479.
Guenthner et al., "A new silicon-containing bis(cyanate) ester resin with improved thermal oxidation and moisture resistance," Macromol. vol. 3 (2006) 6046-6053.
Hay et al., "6: Processing and cure schedules for cyanate ester resins," Chem & Tech Cyanate Ester Resins (1994) 22 pages total.
Marella et al., "An investigation on the hydrolysis of polyphenolic cyanate esters using near-IR spectroscopy," Drexel University Thesis, (2008) 102 pages total.
Maya et al., "Oligodimethylsiloxane linked cyanate ester resins," Macromol., vol. 35 (2009) 460-466.
Shimp et al., "Moisture effects and their control in the curing of polycyanate resins," ACS PMSE Prepr., vol. 66 (1992) 504-505.
Shimp et al., "Cyanate esters—a new family of high temperature thermosetting resins," High Temp. Polym. (1989) 127-140.
Wright, "The synthesis of new silane based bis(cyanate) ester monomers for use in high performance composite resins," Polym. Preprint., vol. 45 (2004) 2 pages total.
Yameen et al., "Polycyanurate thermoset networks with high thermal, mechanical, and hydrolytic stability based on liquid multifunctional cyanate ester monomers with bisphenol A and AF units," Macromol. Chem. Phys., vol. 209 (2008) 1673-1685.
McOnnell, "Resins for the hot zone, part I: polyimides," Composites World (2009) 6 pages total.
McOnnell, "Resins for the hot zone, part II: BMIs, CEs, benzoxazines and phthalonitriles," Composites World (2009) 6 pages total.
United States Patent and Trademark Office, Non-Final Office Action in Application No. 113/748,730, mailed Jul. 22, 2014, 8 pages.

\* cited by examiner

PERIPHERALLY AROMATIC SILSESQUIOXANES FEATURING REACTIVE FUNCTIONALITY: SYNTHESIS AND APPLICATIONS THEREOF

CROSS REFERENCE TO RELATED APPLICATION

This application claims priority of the filing date of provisional application Ser. No. 61/374,669 filed on Aug. 18, 2010.

RIGHTS OF THE GOVERNMENT

The invention described herein may be manufactured and used by or for the Government of the United States for all governmental purposes without the payment of any royalty thereon.

FIELD OF THE INVENTION

This invention relates to synthesis methods and applications for the production and use of organic/inorganic hybrid polyhedral oligomeric silsesquioxane (POSS) nanomaterials.

BACKGROUND OF THE INVENTION

The dispersion of nanoscopic particles in host polymers has resulted in well-documented improvements in various properties, such as thermo-oxidative stability, response to mechanical load, thermal expansion, space survivability, abrasion resistance, moisture uptake, electrical characteristics, and other surface-related properties. As a result, the application of nanotechnology has enabled an expansion in the end-use envelope of many organic materials. Nanoparticles classified as polyhedral oligomeric silsesquioxanes, or POSS, have proven to be a particularly effective class of additives due to their inherent size, shape, rigidity, and versatility in function. The ability to chemically tailor POSS through synthetic manipulation over its organic periphery offers a unique design tool for controlling particle affinity and resultant dispersion in host materials. The number of peripheral substituents is dependent on the size of the silsesquioxane cage itself, or more precisely, the number of silicon atoms contained within the cage. The nature of those substituents may be depends on the limitations defined by state-of-the-art POSS synthesis methods. There are advantages and disadvantages in the choice of an inert or reactive periphery. In general, inert functionalities do not require an adjustment of polymerization stoichiometry or impose complications arising from differences in the reaction kinetics amongst the involved chemical species; however, inert functionalities provide limited control in the formation of desired material morphologies and increased possibility for nanoparticle flux to a more desired energy state over time that may result in a possible degradation of properties during such a process. Reactive moieties, on the other hand, allow for more precise control over copolymer architecture and impede nanoparticle migration over time (due to covalent attachment to the host); however, reactive moieties stoichiometric balance that is often hindered by steric restraints. A review of the current state of inert and reactive POSS technologies may be found in Fina, A. et al., *Journal of Materials Chemistry* 2010, 20(42), 9297-9305. Overall, selection of the POSS periphery should be based on the structure of the polymer that is intended to be modified and the desired end-use properties.

To date, an array of POSS molecules have been developed for a variety of applications. While POSS is useful as a commercial additive, there are currently some limitations in its utility. The limitations are especially true in the modification of high temperature polymers, due to a general weakness in the thermal stability of organic peripheries with C—C bonds having dissociation energies in the close proximity of 80 kcal/mol. Currently, the most thermally robust versions of POSS have cages functionalized with complete inert aromaticity. Examples include Octaphenyl™ and Dodecaphenyl™ POSS, which feature pure phenyl moieties comprised of C═C bonds having dissociation energies of approximately 150 kcal/mol. Unfortunately, such molecules demonstrate a propensity to crystallize to the extent that their assembled aggregation is unaffected by shear forces imposed by conventional polymer blending and compounding methods. Crystallization is also to the extent that the exemplary POSS cages degrade during the melting process, both characteristics preventing effective dispersion into host materials. From a structural perspective, POSS molecules readily crystallize due to the rigid and regular nature of the silsesquioxane cage itself. This propensity for crystallization has been shown to be disrupted through the design and synthesis of a heterogeneous organic periphery, which is described in Moore et al., *Journal of Organometallic Chemistry* 2011, 696(13), 2676-2680. The achievement of a balance between good thermal stability and dispersability lies in molecular design.

To maximize the full benefits of POSS incorporation into polymer hosts, such as in terms of the delivered composite properties, the POSS molecules design requires consideration of molecular assembly during incorporation into a polymer host. For POSS molecules possessing a reactive or partially reactive periphery, geometric forethought of the attachment route with a polymer host network is necessary. For example, POSS may be incorporated through copolymerization by strategic placement of the silsesquioxane cage in the main chain ("bead-on-a-string") of a growing polymer chain or network, as described in U.S. Pat. No. 6,767,930, issued To Svejda et al. in 2004, or conversely, in a pendant, or dangling-type conformation, such as is described in Wright et al., *Macromolecules* 2006, 39(14), 4710-4718. The resulting architectures often yield a marked difference in morphology and as a result, in delivered properties.

In terms of imparting reactive functionality to POSS, amine groups offer the most versatility due to their compatibility with many types of polymers, viz. epoxies, cyanate esters, and polyimides (both thermoplastic and thermosetting in nature). Twelve varieties of amino-containing POSS molecules are commercially available, however, all but one of those compounds contain peripheries comprised of thermally labile chemical groups, i.e., any combinations of isobutyl, isooctyl, cyclohexyl, ammonium, aminoethyl, and aminopropyl groups. POSS molecules have been used to modify various polymers, which are the subject of various patents. In the high temperature polymer area, for example, polyimides have been modified with aminopropylisobutyl POSS in Poe, et al. U.S. Application Publication Nos. 2009/0069508 (2008) and 2010/0063244 (2009). These types of moieties, in general, pose a thermal and solubility mismatch with polymers considered to be high temperature (largely aromatic). Disassociation of the POSS organic periphery can produce free radicals that may react with any polymer in the immediate vicinity, thus causing chain scission and property weakening. The sole commercial compound that possesses a thermally stable, homogeneous aniline periphery has the drawback of possessing a high density of reactive groups. When reactively is incorporated into a polymer, this characteristic generally contributes to either the formation of an over-crosslinked network resulting in material embrittlement or incomplete amine conversion (due to steric barriers resulting in sites that exhibit an affinity to water, which are deleterious toward material aging manifested in thermo-mechanical properties). Therefore, there exists a significant need for the development of new, thermally stabile, amino-functionalized POSS compounds with a lower concentration of reactive groups. Such molecules would be beneficial in the design and control of polymeric architectures for the purposes of maximizing delivered properties, especially at elevated temperatures. Further utility of the embodied aniline POSS compounds is readily derived from chemical reaction of their amine groups with anhydride compounds to form imide-type moieties with other types of reactive end-groups, notably phenylethynyl phthalic anhydride (PEPA) (a crosslinkable group found on the ends of many high performance thermosetting oligomeric compounds). Crosslinking proceeds during consumption of the ethynyl group through cyclotrimerization to form a thermally and mechanically robust aromatic junction.

Figure 7:
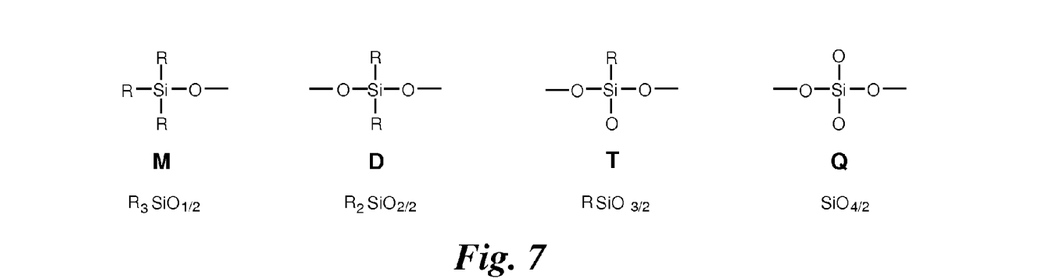
FIG. 7 is an example of silicon atom nomenclature, describing M-, D-, T-, and Q-type silicon atoms.

The nomenclature for silicon atoms was originally developed to distinguish silicon monomers and polymers. A silane (M) group consists of three organic groups and one oxygen atom bound to a central silicon atom. A siloxane (D) group consists of two organic groups and two oxygen atoms bound to the central silicon atom. When one organic group and three oxygen atoms bound to a central silicon atom, the group is referred to as a silsesquioxane (T) group. A silicate (Q) group consists of four oxygen atoms bound to the central silicon atom, which is not bound to any organic groups. The structure of each group is illustrated below. This method allows the simplified description of various structures.

SUMMARY OF THE INVENTION

The present invention describes previously unreported versions of POSS mono- and dianilines that feature completely aromatic peripheries for the purpose of matching the thermal and chemical capabilities of the POSS compound with high performance polymeric materials. Incorporation of these POSS mono- or dianilines into polymer hosts occurs through chemical reaction of amine moieties of the POSS compound with a variety of functionalities, including epoxies, anhydrides, and cyanate esters. The amine groups may also be further reacted with phenylethynyl phthalic anhydride (PEPA) to yield POSS monomers useful as drop-in additives for high temperature thermosets, also possessing PEPA in their chemical structure. Resulting POSS-containing polymers generally exhibit improved processing and delivered properties.

DETAILED DESCRIPTION OF THE INVENTION

This invention describes syntheses and applications of novel polyhedral oligomeric silsesquioxane (POSS) anilines and anhydride-modified derivatives thereof. The POSS compounds exhibit complete aromaticity in their heterogeneous organic peripheries. The POSS anilines may include: (1.) a "bead-type" silsesquioxane diamine possessing 10 silicon atoms and 14 oxygen atoms, wherein 8 of the silicon atoms are considered T silicon atoms (covalently attached to 3 oxygen atoms) and two of the silicon atoms are D silicon atoms attached to 2 oxygen atoms with the anilines placed in the meta position relative to the attachment of the phenyl groups to the D silicon atoms; (2.) heteroleptically phenyl POSS T8 monoaniline isomers, where the amine group is attached in the para or meta position relative to the attachment of the phenyl group to a T silicon atom; (3.) "bead-type" silsesquioxanes with the aniline groups either in the para or meta position relative to the D silicon atoms, where the amine groups are reacted with phenylethynyl phthalic anhydride (PEPA) to form phenylethynyl phthalic imide (PEPI) POSS molecules; and (4.) the POSS T8 monoaniline isomers, or any mixture thereof, reacted with PEPA to form T8 mono-functional T8 PEPI. Other embodiments are directed to a method of synthesizing an existing double-decker (T8D2) silsesquioxane diamine with the dianiline groups in the para position relative to the D silicon atoms. The uniqueness of the disclosed materials is their design for controlled incorporation into polymers that can withstand continuous service at 200-350° C. in an oxygen-rich environment (that is, high temperature polymers). In terms of chemical architecture, the POSS compounds of the present invention feature silsesquioxane cages surrounded by only phenyl and aniline moieties. POSS cages having aniline moieties are equipped for facile attachment to host systems that accept amines through chemical reaction. The reactions include, for example, polyimides through linear copolymerization and epoxies where the amines can participate in network formation through crosslinking. Complete peripheral aromaticity and a lack of thermally labile groups enable exceptional thermal stability for POSS anilines and good solubility (high optical clarity) in high temperature polymers.

Copolymerization of these types of POSS molecules with thermoplastic or thermosetting polymer systems that accept amines during chemical reaction or ethynyl groups through cyclotrimerization, viz. monomers, oligomers, or polymers having epoxide groups, anhydride groups, cyanate ester groups, or ethynyl groups, are anticipated to improve processability, short- and long-term thermo-oxidative stability, abrasion resistance, mechanical properties such as toughness, creep, coefficient of thermal expansion and tensile strength, solvent resistance, dielectric properties, and reductions in thermal expansion, moisture uptake, flammability and heat of combustion, and hydrophobicity.

EXAMPLES

1. Synthesis of Phenyl$_7$ POSS Monoaniline

Synthesis of monoamine precursor, p-Cl$_3$Si[PhN(TMS)$_2$]: A solution of 4-Bromo-N,N-bis(trimethylsilyl)aniline (9.48 g, 30 mmol) in 25 mL of anhydrous THF is taken in an addition funnel and slowly added to a stirring mixture of Mg (0.912 g, 38 mmol) and anhydrous THF initiated with a crystal of I$_2$ and a drop of 4-bromo-N,N-bis(trimethylsilyl) aniline. The reaction is allowed to stir overnight at ambient temperature, cannulated into a 250 mL round bottomed flask, and very slowly added to a stirring mixture of THF (10 mL) and silicon tetrachloride (5.35 g, 31.5 mmol). This is allowed to stir overnight. The solvent is removed, in vacuo, from the reaction mixture and dry hexane added to extract the product by filtration through celite. After removing all volatiles under a dynamic vacuum, the residual yellow colored filtrate is transferred to a 25 mL flask and distilled under dynamic vacuum to give phenyl-bis(trimethylsilyl)trichlorolsilane, as a colorless, very viscous liquid in 90% yield. $^1$H NMR (CDCl$_3$) 0.136 ppm (s, 18H, NSiCH$_3$), 7.08 ppm (m, 4H), 7.73 ppm (m, 4H). $^{29}$Si NMR (CDCl$_3$) 5.81 ppm, −0.475 ppm (ratio=2:1)

Synthesis of POSS monoamine: a solution of phenyl-bis (trimethylsilyl)trichlorolsilane precursor (0.89 g, 2.4 mmol), in 5 mL dry ether is added very slowly to a stirring solution of trisilanolphenyl-POSS, Ph$_7$Si$_7$O$_9$(OH)$_3$ (2.06 g, 2.2 mmol) in 10 mL dry ether and 5 mL anhydrous THF. To this is very slowly added a solution of distilled triethylamine in dry ether (0.6966 g, 6.90 mmol). This is left stirring over night. The solution is filtered to remove NEt$_3$. HCl precipitates and rotary evaporated to slurry. The slurry is precipitated fully in 150 mL reagent grade methanol acidified with glacial acetic acid to give POSS monoamine monomer in 60% yield. $^{29}$Si NMR (CD$_2$Cl$_2$) −76.99 ppm, −78.34 ppm, −78.50 ppm (ratio=1:4:3).

2. Synthesis of Phenyl$_7$ POSS Mono-phenylethynyl Phthalic Imide

In a 50 mL round bottom flask, a solution of PEPA (0.246 g, 1 mmol) in 35 mL toluene is added to a stirring solution of POSS phenylamine (1.05 g, 1 mmol) in 5 mL dimethylacetamide (DMAC). This is attached to a reverse Dean Stark apparatus, which is dried in an oven, evacuated, and backfilled with GN2 prior to use. The entire set up is equipped with a condenser and a thermometer. The stirring reaction mixture is heated in an oil bath at 1500° C. for 6 hr and allowed to cool to room temperature. White precipitates obtained at the bottom of the reaction flask are filtered, washed with anhydrous diethyl ether, and air dried under nitrogen for 6 hr. These are further dried under vacuum at 1200° C. for 24 hr. 29Si NMR (CDCl$_3$) −78.07 ppm, −78.16 ppm, −78.67 ppm (ratio=3:4:1).

3. Synthesis of Bis(Meta-aniline, Methyl)Silyloxy-octaphenylsilsesquioxane ("Bead-type" POSS Dianiline)

Under a nitrogen atmosphere, in a 50 mL round-bottomed flask phenylPOSS-tetrol, Phenyl$_8$Si$_8$O$_{10}$(OH$_4$), (2.00 g, 1.87 mmol) is suspended in 10 mL of anhydrous THF. To this stirred suspension, a solution of 3-[bis(N,N-trimethylsilyl) phenylamino]methyldichlorosilane (1.376 g, 3.93 mmol) and NEt$_3$ (0.776 g, 7.67 mmol) in THF (10 mL) is slowly added in a drop-wise manner. After 30 min, the solution is filtered to remove NEt$_3$HCl (957 mg, 6.95 mmol, 93% theoretical) and the solvent is removed under vacuum. Approximately 1 mL of diethylether is added to the product followed by 20 mL of MeOH to make a well-stirred suspension of white-colored intermediate. The trimethylsilyl groups are hydrolyzed by the addition of 1 drop of concentrated acetic acid and 1 hr of stirring. The product is isolated by filtration and dried under a nitrogen stream to give a white powder in 84% yield (2.097 g, 1.57 mmol). $^1$H NMR (CDCl$_3$, δ) 7.62-6.99 ppm (m, 44H), 6.74 ppm (m, 4H), 3.3 ppm (broad s, 4H, NH2), 0.58 ppm (s, 6H). $^{29}$Si NMR (CDCl$_3$) −30.5 ppm, −78.4 ppm, −79.4 ppm, −79.6 ppm, −79.8 ppm.

4. Synthesis of Bis(Para-aniline, Methyl)Silyloxy-octaphenylsilsesquioxane ("Bead-type" POSS Dianiline)

Synthesis of 4-[Bis(N, N-trimethylsilyl)phenylaminio] methyldichlorosilane precursor: under a nitrogen atmosphere a solution of 4-bromo-N, N-bis(trimethylsilyl)aniline (9.48 g, 30 mmol) in 25 mL of anhydrous THF was placed in an addition funnel and slowly added to a stirring mixture of Mg (0.912 g, 38 mmol) and anhydrous THF, already initiated with a small crystal of I$_2$ and a drop of 4-bromo-N,N-bis(trimethylsilyl)aniline. The reaction was allowed to stir overnight at ambient temperature, then slowly cannulated into a 250 mL round-bottomed flask containing a stirring mixture of THF (10 mL) and methyltrichlorosilane (4.485 g, 30 mmol). This was allowed to stir overnight. The solvent was removed, in vacuo, from the reaction mixture and dry hexane added to extract the product by filtration through celite. After removing all volatiles under vacuum at room temperature, the remaining yellow-colored filtrate was transferred to a 25 mL flask. This was distilled at 89° C. under dynamic vacuum using a Kugelrohr apparatus to give the product as a colorless liquid in 87% yield (9.15 g, 26.1 mmol). $^1$H NMR (CDCl$_3$) 0.13 ppm (s, 18H, NSiCH3), 1.06 ppm (s, 3H, SiCH3), 7.03 ppm (m, 2H), 7.61 ppm (m, 2H). $^{29}$Si NMR (CDCl$_3$, δ) 5.2 ppm, 18.9 ppm (ratio=2:1).

Figure 1:
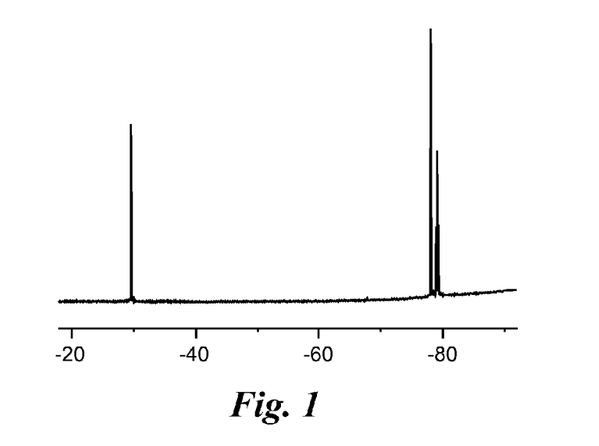
FIG. 1 is NMR spectrum of bis(para-aniline, methyl)silyloxy-octaphenylsilsesquioxane ("bead-type" POSS).
Figure 2:
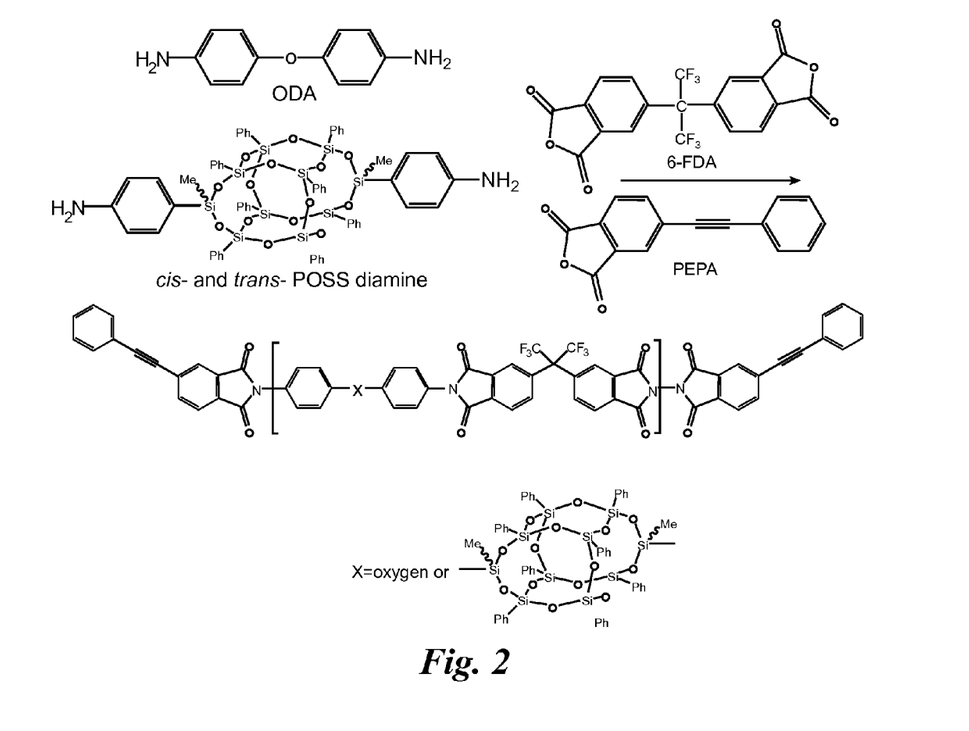
FIG. 2 is chemical structures of monomers and resultant oligoimides resulting from systematic modification of the condensation oligomer 6FDA-ODA-PEPA by substitution of ODA with "bead-type" POSS.
Figure 3:
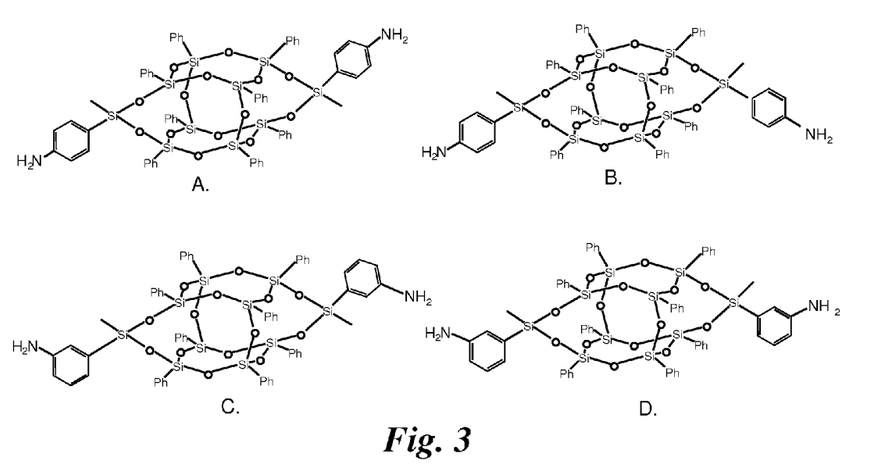
FIGS. 3A-3D exhibit representations of the chemical structures of the various conformations that "bead-type" POSS dianilines can adopt, including: trans-bis(para-aniline, methyl)silyloxy-octaphenylsilsesquioxane in FIG. 3A, cis-bis(para-aniline, methyl)silyloxy-octaphenylsilsesquioxane in FIG. 3B, trans-bis(meta-aniline, methyl)silyloxy-octaphenylsilsesquioxane in FIG. 3C, and cis-bis(meta-aniline, methyl)silyloxy-octaphenylsilsesquioxane in FIG. 3D.
Figure 4:
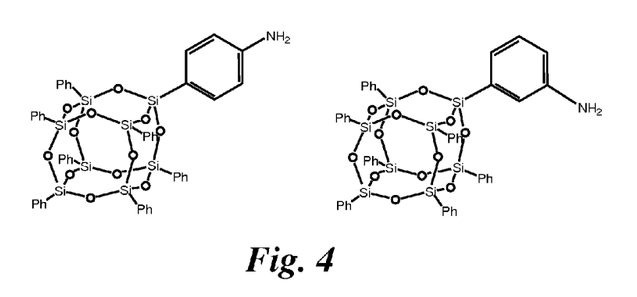
FIG. 4 illustrates chemical structures of heptaphenyl-monoaniline-T8 POSS with amine functionality either in the para or meta position relative to phenyl group attachment to the Si atom.
Figure 5:
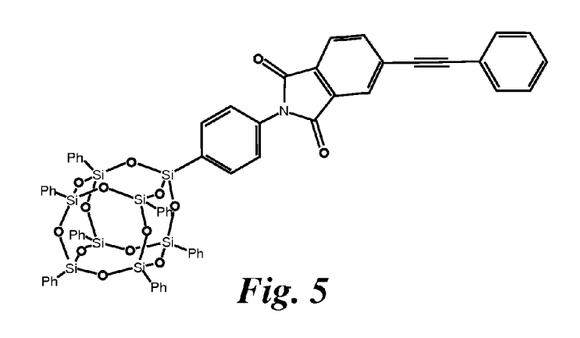
FIG. 5 illustrates the chemical structure for heptaphenyl-monoaniline-T8 POSS reacted with phenylethynyl phthalic anhydride (PEPA) to form phenylethynyl phthalimide (PEPI), wherein the PEPI functionality can either be in the para or meta position relative to phenyl group attachment to the Si atom.
Figure 6:
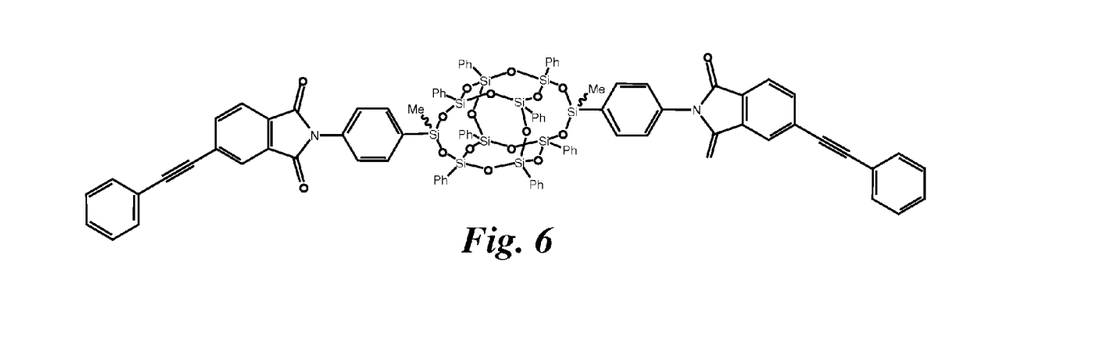
FIG. 6 is an example of the reaction product between a "bead-type" POSS isomer and PEPA.

Synthesis of Bis(para-aniline, methyl)silyloxy-octaphenylsilsesquioxane: under a nitrogen atmosphere, in a 50 mL round-bottomed flask phenyl POSS-tetrol, Phenyl$_8$Si$_8$O$_{10}$(OH$_4$), (2.00 g, 1.87 mmol) was suspended in 10 mL of anhydrous THF. To this stirred suspension, a solution of 4-[bis(N, N-trimethylsilyl)phenylaminio]methyldichlorosilane (1.376 g, 3.93 mmol) and NEt$_3$ (0.776 g, 7.67 mmol) in THF (10 mL) was slowly added in a drop-wise manner. After 30 min, the solution was filtered to remove NEt$_3$HCl (974 mg, 7.08 mmol, 95% theoretical) and the solvent was removed under vacuum. Approximately 1 mL of diethylether was added to the product followed by 20 mL of MeOH to make a well-stirred suspension of white-colored intermediate. The trimethylsilyl groups were hydrolyzed by the addition of 1 drop of concentrated acetic acid and 1 hr of stirring. The product was isolated by filtration and dried under a nitrogen stream to give a white powder in 77% yield (1.922 g, 1.44 mmol). $^1$H NMR (CDCl$_3$, δ) 7.83-7.10 ppm (m, 44H), 6.60 ppm (m, 4H), 3.3 ppm (broad s, 4H, NH2), 0.11 ppm (s, 6H). $^{29}$Si NMR (CDCl3) −29.7 ppm, −78.2 ppm, −79.1 ppm, −79.3 ppm, −79.4 ppm (reference spectrum in FIG. 1).

5. Application of POSS Monoaniline for the Purposes of Thermosetting Polymer Modification To modify a conventional epoxy resin/aminated hardener system with POSS monoaniline, a mixture of amines is employed to cure the epoxy adhesive. In the specific example of DER 331 epoxy, having an epoxide equivalent weight of 189, cured with 4-4'-dimanodiphenyl sulfone (DDS) possessing an amine H equivalent weight of 64, modified with 5% POSS monoaniline to 95% DDS in the amine mixture:

$$\text{Amine } H \ eq \cdot wt \cdot POSS = \frac{544}{2} = 272$$

$$phr \ \text{Amine} = \frac{272 \times 100}{189} \times 0.05 + \frac{64 \times 100}{189} \times 0.95 = 39.37$$

phr POSS monoaniline amine=7.2 phr DDS=32.2

To 100 g DER 331 epoxy, 39.37 g DDS, and 7.2 g POSS monoaniline are added and are homogenized with or without the use of a common solvent. If solvent is used, it is driven off by vacuum drying at elevated temperature. The resulting resin may be cured with our without the use of pressure using the appropriate cure protocol for DDS. Alternatively, the resin may be used as an application to continuous fibers, such as graphite, to produce a prepreg material for use in composite material fabrication.

6. Application of "Bead-type" POSS Dianiline for the Modification of a Thermosetting Oligomer According to the molar equivalents and weights of monomers shown in Tables 1 and 2, respectively, 6-FDA monomer was added to an NMP solution of ODA and/or POSS in a dry nitrogen environment. After allowing the reaction to proceed for 60 min, an NMP solution of PEPA was then added to produce a total concentration of 10 wt % solids. The reaction was allowed to stir overnight in a dry nitrogen environment. 15 mL of toluene was added and the reaction was heated to 155° C. using the Dean-Stark methodology to promote imidization. FTIR is used to ensure the achievement of full imidization. A solvent extraction to separate NMP from oligomer was then performed using 15 mL of chloroform and distilled water. Excess chloroform was removed under reduced pressure; the reaction mixture was then added dropwise to methanol and allowed to stir overnight. The solid product was collected by filtration and washed with methanol. The solid product was dried under vacuum and subsequently characterized by $^1$H, $^{13}$C, and $^{29}$Si NMR.

TABLE 1

Equivalents of monomers used to synthesize each of the oligoimides.

| Compound Mol. Wt. Formula | PEPA 248.23 C$_{16}$H$_8$O$_3$ | 6-FDA 444.24 C$_{19}$H$_6$F$_6$O$_6$ | ODA 200.24 C12H12N2O | POSS 1335.98 C$_{62}$H$_{58}$N$_2$O$_{14}$Si$_{10}$ |
|---|---|---|---|---|
| 0 POSS | 2 | 4 | 5 | 0 |
| 1 POSS | 2 | 4 | 4 | 1 |
| 2 POSS | 2 | 4 | 3 | 2 |
| 3 POSS | 2 | 4 | 2 | 3 |
| 4 POSS | 2 | 4 | 1 | 4 |
| 5 POSS | 2 | 4 | 0 | 5 |

TABLE 2

Amounts of monomers used in each of the six oligoimides.

| Target Oligomer (Avg. mol. for.) | Molecular Weight | Mmoles in 7.00 g | PE (g) | 6-FDA (g) | ODA (g) | POSS (g) | Wt. % Si$_{10}$O$_{14}$ |
|---|---|---|---|---|---|---|---|
| C$_{168}$H$_{80}$F$_{24}$N$_{10}$O$_{25}$ | 3094.45 | 2.2624 | 1.1228 | 4.0194 | 2.2645 | 0.000 | 0.0% |
| C$_{218}$H$_{126}$F$_{24}$N$_{10}$O$_{38}$Si$_{10}$ | 4230.19 | 1.6548 | 0.8218 | 2.9407 | 1.3251 | 2.2106 | 8.33% |
| C$_{268}$H$_{172}$F$_{24}$N$_{10}$O$_{51}$Si$_{20}$ | 5365.94 | 1.3048 | 0.6475 | 2.3184 | 0.784 | 3.4853 | 13.16% |
| C$_{318}$H$_{218}$F$_{24}$N$_{10}$O$_{64}$Si$_{30}$ | 6501.69 | 1.0766 | 0.5348 | 1.9131 | 0.262 | 4.3148 | 16.31% |
| C$_{368}$H$_{264}$F$_{24}$N$_{10}$O$_{77}$Si$_{40}$ | 7637.44 | 0.9163 | 0.4550 | 2.3289 | 0.1834 | 4.8979 | 18.48% |
| C$_{418}$H$_{310}$F$_{24}$N$_{10}$O$_{90}$Si$_{50}$ | 8773.18 | 0.798 | 0.3962 | 1.4175 | 0.000 | 5.3298 | 20.16% |

7. Application of "Pendant-type" PEPI POSS to the Modification of a Thermosetting Oligomer To 10 g of a thermosetting oligomer powder comprised of repeat units consisting of the monomers 6-FDA and ODA, end-capped with PEPA, 10 percent by weight, or 1.11 g of "bead-type" PEPI POSS powder is added. The resultant binary powder mixture may be homogenized by (A.) melt blending with conventional polymer blending and compounding equipment between the temperatures of 220° C. and 270° C. for 5 min followed by injection into an appropriately shaped mold and cured under a pressure of 100 psi at 371° C. for 1 hr, or (B.) dissolving the resultant binary powder mixture in a common solvent, such as NMP, at a solute concentration of 10 percent by weight, and precipitated with the use of a common non-solvent, such as methanol. The resultant powder is isolated and dried. The isolated material may be compression molded in purely resin form at 100 psi and cured, in-situ, at 371° C. for 1 hr. Alternatively, the co-solution of the binary mixture may be used as an application to continuous fibers, such as graphite, and the majority of the solvent may be driven off using an oven, to produce a prepreg material for use in composite material fabrication.

What is claimed is:

1. A polyhedral oligomeric silsesquioxane comprising:
an inorganic core comprising:
6-14 silicon atoms, at least one of the silicon atoms being an M-type silicon atom or a D-type silicon atom, and at least one of the silicon atoms being a T-type silicon atom; and
9-20 oxygen atoms;
a cycloaromatic group covalently coupled to the at least one T-type silicon atom, wherein the cycloaromatic group is a naphthyl group, a phenanthrenyl group, an anthracenyl group, or a pyrenyl group; and
a phthalic imide derivative covalently coupled to the at least one D-type silicon atom or the at least one M-type silicon atom.

2. A polyhedral oligomeric silsesquioxane comprising:
an inorganic core comprising:
6-14 silicon atoms, at least one of the silicon atoms being an M-type silicon atom or a D-type silicon atom, and at least one of the silicon atoms being a T-type silicon atom; and
9-20 oxygen atoms;
a cycloaromatic group covalently coupled to each of the at least one T-type silicon atoms; and
an aromatic derivative, having at least one nitrogen atom therein, covalently coupled in a meta-position to the at least one D-type silicon atom or the at least one M-type silicon atom.

3. The polyhedral oligomeric silsesquioxane of claim 2, wherein the cycloaromatic group is a phenyl group and the aromatic derivative is a phthalic imide derivative.

4. The polyhedral oligomeric silsesquioxane of claim 2, wherein the cycloaromatic group is selected from the group consisting of a phenyl group, a naphthyl group, a phenanthrenyl group, an anthracenyl group, and a pyrenyl group.

5. The polyhedral oligomeric silsesquioxane of claim 2, wherein the aromatic derivative is selected from the group consisting of a phenyl group, an aniline group, and a phthalic imide derivative.

6. The polyhedral oligomeric silsesquioxane of claim 1, wherein the aromatic derivative covalently coupled to the at least one D-type silicon atom or the at least one M-type silicon atom is in the meta-position.

7. A polyhedral oligomeric silsesquioxane comprising:
an inorganic core comprising 6-14 silicon atoms, including an M-type silicon atom or a D-type silicon atom and a T-type silicon atom and 9-20 oxygen atoms;
a cycloaromatic group covalently coupled to the T-type silicon atom, wherein the cycloaromatic group selected from the group consisting of a naphthyl group, a phenanthrenyl group, an anthracenyl group, and a pyrenyl group; and
an aromatic derivative, having at least one nitrogen atom therein, covalently coupled in a meta-position to the D-type silicon atom or the M-type silicon atom.

8. The polyhedral oligomeric silsesquioxane of claim 2, wherein the cycloaromatic group is selected from a group comprising of a phenyl moiety and an aniline moiety and the aromatic derivative is a meta-aniline group or a para-aniline group.

9. The polyhedral oligomeric silsesquioxane of claim 2, wherein the polyhedral oligomeric silsesquioxane is a dianiline having the formula:

wherein the symbol Ph is representative of the cycloaromatic group and the symbol Me is representative of a methyl group.

10. The polyhedral oligomeric silsesquioxane of claim 2, wherein the cycloaromatic group is a phenyl group and the aromatic derivative is a meta-aniline group or a para-aniline group.

* * * * *